United States Patent
Oddie et al.

(10) Patent No.: US 8,857,245 B2
(45) Date of Patent: Oct. 14, 2014

(54) SYSTEM AND METHOD FOR MEASURING OR MONITORING OF A LOW CONCENTRATION DISPERSED PHASE

(75) Inventors: Gary Oddie, St. Neots (GB); Michel Berard, Paris (FR); Michael John Williams, Ely (GB)

(73) Assignee: Schlumberger Technology Corporation, Sugar Land, TX (US)

( * ) Notice: Subject to any disclaimer, the term of this patent is extended or adjusted under 35 U.S.C. 154(b) by 556 days.

(21) Appl. No.: 12/809,386

(22) PCT Filed: Dec. 17, 2008

(86) PCT No.: PCT/GB2008/004165
§ 371 (c)(1),
(2), (4) Date: Oct. 14, 2010

(87) PCT Pub. No.: WO2009/077754
PCT Pub. Date: Jun. 25, 2009

(65) Prior Publication Data
US 2011/0041590 A1    Feb. 24, 2011

Related U.S. Application Data

(60) Provisional application No. 61/015,121, filed on Dec. 19, 2007, provisional application No. 61/015,134, filed on Dec. 19, 2007.

(51) Int. Cl.
*G01N 29/00* (2006.01)
*G01N 5/02* (2006.01)
*G01N 33/28* (2006.01)
*G01N 29/036* (2006.01)
*G01N 9/00* (2006.01)
*G01N 30/02* (2006.01)

(52) U.S. Cl.
CPC ........ *G01N 5/02* (2013.01); *G01N 2291/02809* (2013.01); *G01N 33/28* (2013.01); *G01N 2291/0256* (2013.01); *G01N 29/036* (2013.01); *G01N 33/2847* (2013.01); *G01N 5/025* (2013.01); *G01N 9/002* (2013.01)

USPC .......................... 73/61.49; 73/64.53; 73/61.79

(58) Field of Classification Search
CPC ... G01N 11/16; G01N 29/036; G01N 29/022; G01N 2291/0256; G01N 9/002
USPC ............ 73/54.23, 54.24, 54.25, 54.26, 54.27, 73/54.28, 54.29, 54.31, 54.32, 54.33, 73/54.34, 54.41, 61.49, 61.79, 61.72, 73/61.73, 61.75, 64.53, 861.21, 861, 32 A
See application file for complete search history.

(56) References Cited

U.S. PATENT DOCUMENTS 4,129,501 A   12/1978   Haynes
4,562,725 A   1/1986    Oka et al.
(Continued)

FOREIGN PATENT DOCUMENTS

EP   0022444   1/1981

OTHER PUBLICATIONS

Manrique: "Development of an integrated model of a vibrating element fluid property sensor", PhD Thesis, Imperial College, University of London, Apr. 2005, pp. 127-141.

(Continued)

*Primary Examiner* — Daniel S Larkin
*Assistant Examiner* — Jamar Ray

(57) ABSTRACT

Systems and methods are disclosed for measuring and/or monitoring concentrations of a dispersed phase in a fluid. A wettable surface may be used that is configured to be selectively wettable by the dispersed phase in the fluid being tested/monitored and the amount of or the rate of change of the wetting/deposition of the dispersed phase on the wettable surface is sensed and used to monitor the concentration of the dispersed phase.

15 Claims, 6 Drawing Sheets

(56) References Cited

U.S. PATENT DOCUMENTS

| | | | |
|---|---|---|---|
| 5,571,944 | A | 11/1996 | Pfeifer et al. |
| 7,143,638 | B1 * | 12/2006 | Scott .............................. 73/61.43 |
| 7,617,055 | B2 * | 11/2009 | Henry et al. ..................... 702/48 |
| 7,775,085 | B2 * | 8/2010 | Scott .............................. 73/61.43 |
| 7,935,191 | B2 * | 5/2011 | Mutharasan et al. ............. 134/1 |
| 2005/0052813 | A1 | 3/2005 | Kobayashi |
| 2005/0145019 | A1 * | 7/2005 | Matsiev et al. ............... 73/53.01 |
| 2006/0123910 | A1 * | 6/2006 | Cunningham et al. .......... 73/580 |

OTHER PUBLICATIONS

Wenzel et al: "Flexural plate-wave gravimetric chemical sensor", Sensors and Actuators A: Physical, Elsevier, vol. A21A23, 1990, pp. 700-703.

International Search Report of PCT Application No. PCT/GB2008/004165 dated May 4, 2009.

* cited by examiner

SYSTEM AND METHOD FOR MEASURING OR MONITORING OF A LOW CONCENTRATION DISPERSED PHASE

This application claims the benefit of and is a non-provisional of U.S. Provisional Application Ser. No. 61/015,121 filed on Dec. 19, 2008, which is hereby expressly incorporated by reference in its entirety for all purposes.

This application is related to U.S. Patent Application Ser. No. 61/015,134, filed on the same date as the priority application described above, entitled "System and Method for Fluid Sensing Correction", which is incorporated by reference in its entirety for all purposes.

BACKGROUND OF THE DISCLOSURE

Embodiments of the present invention relate in general to measuring concentrations of dispersed phases in a flowing mixture. More specifically, but not by way of limitation, embodiments of the present invention provide for selectively wetting and/or coalescing the dispersed phase onto a sensor, measuring deposition and/or a rate of increase of an amount of the dispersed phase collected on the sensor and using the amount of deposition and/or the rate of collection of the dispersed phase on the sensor to determine or monitor a concentration of the dispersed phase in the flowing mixture.

It is often very important to know/monitor a concentration of constituents/contaminant or the like dispersed in a fluid mixture. For example, environmental regulations may require monitoring of liquid contaminants dispersed in a fluid, such as water or the like. Environmental regulations and laws may require certification from a party seeking to pump a fluid into the environment, such as disposal into a body of water, an underground formation, an underground reservoir and/or the like, regarding the purity and/or amount of contamination of liquids being introduced/re-introduced into the environment. As such, reservoirs, inputs to reservoirs, fluids to be dispersed into the environment and/or the like may need to be monitored/tested to determine the amount of dispersed contaminants within the reservoirs or being dispersed into an environment. For such monitoring/testing/certification purposes, because of the sensitivity of an environment, regulations may often require monitoring/measurement of very small concentrations of dispersed phases in a liquid, where such concentration may be of the order of several to 100s of parts per million.

In the hydrocarbon industry, there are several oilfield applications where it may be useful or legally required to know the concentration of a dispersed phase in a fluid, which fluid may be a flowing fluid. For example, when disposing of water produced from and/or used in a wellbore for producing hydrocarbons, the disposal location may be the sea, a disposal aquifer or an injection zone in the reservoir. Such disposal into the environment may require the water to contain a dispersed phase contamination, which in the case of water associated with an oil well may comprise oil droplets, below a certain threshold. Furthermore, subsurface disposal of such water may require the dispersed phase contamination, often referred to as the oil-in-water concentration, to be below a determined/specified concentration so as to minimize potential injectivity loss due to fouling of the injection zone by the oil. In other aspects of the hydrocarbon industry, initial detection of water being produced from a hydrocarbon wellbore may be important in oil and gas/condensate wells for process and pipeline control. This may be especially true in the latter type of well where hydrate inhibitors such as methanol are added. In such wellbores, poor or non-existent measurements of water content in produced fluid mixtures may lead to very conservative and costly procedures being unnecessarily used.

Existing online liquid contaminant monitoring devices suffer from limitations. These limitations may include the cost of the apparatus, the sensitivity of the sensing apparatus to adverse/hostile conditions, the use of an indirect physical process that requires a fluid calibration to determine a contamination value to arrive at the dispersed phase concentration—such as an oil-in-water concentration, a water-in-oil-concentration and/or the like—the inability to provide an instant measurement of the dispersed phase concentration, poor low concentration sensitivity and/or the like.

Off line measurements of dilute dispersions involve sampling a portion of a fluid followed by contaminant isolation using titration, solvent extraction and/or the like and subsequent measurement of the isolated contaminant. Such offline processes may be costly, cumbersome, time consuming, do not provide for real-time monitoring of a fluid mixture and/or, in the case of the hydrocarbon industry, may not provide for monitoring at the wellsite or at a remote pipeline/reservoir location.

BRIEF SUMMARY OF THE DISCLOSURE

Embodiments of the present invention provide methods and systems for monitoring a dispersed phase in a fluid mixture, where the dispersed phase is a fluid, such as oil or water, that is present in the fluid mixture, which mixture may comprise fluids, such as water and/or oil. The methods and systems use a wettable surface that is configured to be selectively wettable by the dispersed phase. As a consequence of the selective wettability, the dispersed phase in the fluid mixture wets/is disposed on the wettable surface. In the embodiments of the present invention, the rate of change in the amount of the dispersed phase on the wettable surface is determined and a value of the concentration of the dispersed phase in the fluid mixture is processed from this rate of change; the rate of change being proportional to the concentration of the dispersed phase.

In some aspects of the present invention, the rate of change of the dispersed fluid present on the wettable surface may be determined by measuring a change in properties of an electromagnetic beam/signal transmitted into/through the dispersed phase present on the wettable surface. For example, a microwave, optical, ultraviolet, infrared signal and/or the like may be transmitted into the dispersed phase present on the wettable surface and the change in transmission and/or absorption of the signal may be measured. In other aspects, a change in electrical properties, such as conductance, impedance, resistance, capacitance and/or the like may be measured to determine the rate of change of the dispersed phase present on the wettable surface.

In yet other aspects, acoustic properties, changes in acoustic properties may be measured to determine the rate of change of the dispersed phase present on the wettable surface, for example changes in an ultrasonic beam transmitted into/through the dispersed phase present on the wettable surface may be monitored. In some aspects of the present invention, exiting sensors may be modified to be concentration monitors in accordance with the present invention by making a sensing surface of the existing sensor selectively wettable by a dispersed phase to be monitored and using the sensor to measure the rate of change of the dispersed phase present on the sensing surface.

Some embodiments of the present invention provide for in-line measurement and/or monitoring of concentration of a dispersed phase in a fluid. More specifically, but not by way of limitation, an embodiment of the present invention provides for disposing a wettable surface that is configured to be selectively wettable by the dispersed phase in the fluid being tested/monitored and sensing the amount of or the rate of wetting/deposition of the dispersed phase on the wettable surface. In certain aspects of the present invention, the wettable surface is made to oscillate in the fluid and the change/rate of change of the frequency of oscillation is used to determine an amount/rate of change in the amount of the dispersed phase deposited on the wettable surface. The wettable surface may be cleaned in certain aspects by driving the wettable surface to oscillate at a high frequency to dislodge the dispersed phase deposited on the wettable surface.

In one embodiment of the present invention, a flow meter may provide measurements of the flow of the fluid and these flow measurements may be processed along with the amount of dispersed phase collected on the wettable surface and/or rate of change of the buildup of the dispersed phase on the wettable surface to determine/monitor a concentration of the dispersed phase in the fluid. In certain aspects, the cross-sectional area of the wettable surface in contact with the fluid and/or the cross-section of a conduit the fluid is flowing in may be used to determine/monitor the concentration of the dispersed phase.

Embodiments of the present invention provide methods and systems for monitoring and or measuring a concentration of a dispersed in a fluid. In one embodiment of the present invention, a method for monitoring a concentration of a dispersed phase in a flowing fluid mixture is provided, comprising:

contacting a wettable sensing surface with the flowing fluid mixture, wherein the wettable sensing surface is configured to be preferentially wettable by the dispersed phase;

wetting the sensing surface with the dispersed phase;

measuring a rate of change of the dispersed phase wetting the sensing surface; and using the rate of change of the dispersed phase on the sensing surface to monitor the concentration of the dispersed phase.

In another embodiment, a sensor system for measuring a concentration of a fluid component of a flowing fluid mixture is provided, comprising:

means for selectively collecting a portion of the fluid component from the flowing fluid mixture, wherein the selective collection means comprises an active surface with a known surface area, and wherein the active surface is adapted to provide for selective wetting of the sensing surface by the fluid component; and means for determining a rate of change of the amount of fluid component on the active surface.

In yet another embodiment, the present disclosure provides system for measuring a concentration of a fluid component of a fluid mixture, comprising:

a vibrating element having a sensing surface, wherein the sensing surface is configured to provide for selective wetting of the sensing surface by the fluid component;

a driver for driving the vibrating element to oscillate; and a vibration processor configured to processes an oscillation frequency of the vibrating to determine a rate of buildup of the fluid component on the sensing surface.

BRIEF DESCRIPTION OF THE DRAWINGS

The present disclosure is described in conjunction with the appended figures.

Figure 1:
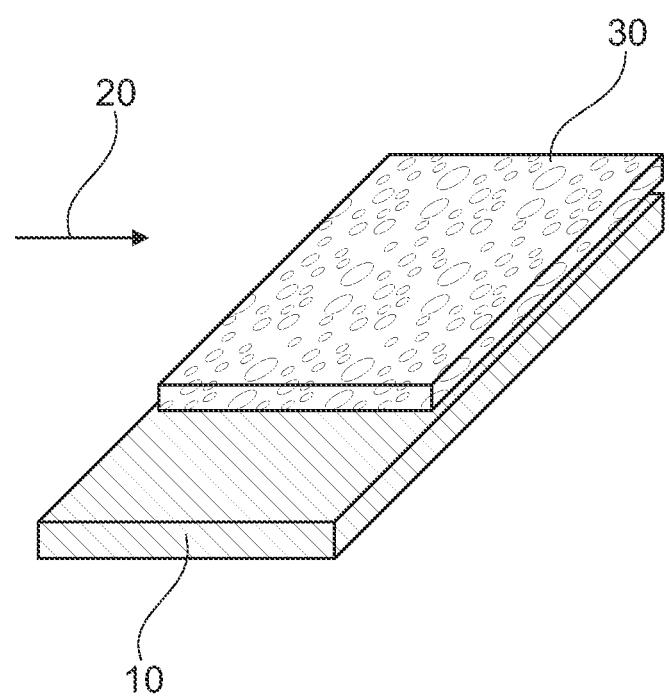
FIG. 1 is a schematic-type diagram of a wettable sensing surface, in accordance with an embodiment of the present invention.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiment(s) only, and is not intended to limit the scope, applicability or configuration of the invention. Rather, the ensuing description of the preferred exemplary embodiment(s) will provide those skilled in the art with an enabling description for implementing a preferred exemplary embodiment of the invention. It being understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments maybe practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc.

When a process corresponds to a function, its termination corresponds to a return of the function to the calling function or the main function.

Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "computer-readable medium" includes, but is not limited to portable or fixed storage devices, optical storage devices, wireless channels and various other mediums capable of storing, containing or carrying instruction(s) and/or data.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine readable medium such as storage medium. A processor(s) may perform the necessary tasks. A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

FIG. 1 is a schematic-type diagram of a wettable sensing surface, in accordance with an embodiment of the present invention. Embodiments of the present invention may make use of wetting forces to provide for determining a concentration of a dispersed phase in a flowing fluid. Wetting forces are a naturally occurring phenomenon, for example, wetting forces cause rain to bead up on waxed cars. Wettability describes the preference of a solid to be in contact with one fluid in contrast to such a preference for other fluids. Wettability is caused by the interplay between surface and interfacial forces.

At a wettable surface, a drop of a preferentially wetting fluid will displace another non-preferentially wetting fluid. In contrast, a non-wetting fluid coming into contact with a wettable surface covered by the wetting fluid will bead up and have minimal contact/interaction with the wettable surface. Different solids and substances with different coating and/or liquids disposed on their surfaces have wettable preferences for different fluids. For example, some solids may be preferentially wettable by water, oil or the like. Moreover, merely by way of example, a solid may be preferentially wettable by water and, essentially, not wettable by oil. As such, a solid may be selected to be wettable by a specific, known and/or desirable fluid. While the preference for a solid/substance to be wettable by a certain fluid is not absolute, a solid/substance may be designated as/possess properties providing a strongly wetting surface for a certain fluid, such as water, oil or the like. Some solids, substances and/or solids with a liquid layer disposed on them may be preferentially wettable by water or the like to a lesser degree than the strongly water or the like wettable surface.

As such, in one embodiment of the present invention, a sensing surface may be coated with or comprise a material that is wettable by a fluid phase of a mixture. For example, by coating the surface or comprising the surface from a hydrophilic compound, the sensing surface of an embodiment of the present invention will be wettable by water. In contrast, by coating the surface or comprising the surface from a hydrophobic compound, the sensing surface of an embodiment of the present invention will be wettable by a fluid in a mixture other than water, such as oil in an oil-in-water mixture. In another embodiment, the sensing surface may be made to be water-wet so that the surface is selectively wettable by water. Merely by way of example, the sensing surface may be made water wet by contacting/coating the sensing surface with water. In an alternative embodiment, the sensing surface may be made to be oil-wet so that the surface is selectively wettable by oil.

In one embodiment of the present invention, a sensing surface 10 is positioned so as to come into contact with a flowing fluid 20. The sensing surface 10 may comprise a material that is strongly preferentially wettable by a specific/certain fluid (hereinafter referred to as "the specific fluid"). In an embodiment of the present invention, the sensing surface 10 may be configured to provide that the specific fluid is a fluid/dispersed phase for which a concentration in the flowing fluid is to be measured/monitored. In certain aspects of the present invention, a coating of the specific fluid may be applied to the sensing surface 10 prior to the sensing surface 10 being contacted with the flowing fluid 20. On other aspects, the sensing surface 10 may be coated with or comprise a compound that is electively wettable by the specific fluid.

The flowing fluid 20 may be flowing in a pipe (not shown) or the like and the sensing surface 10 may be disposed so that at least a portion of the sensing surface 10 contacts the flowing fluid 20 flowing in the pipe. Positioning of the sensing surface 10 in the pipe may depend upon the properties of the specific fluid. Merely by way of example, in some aspects the sensing surface 10 may be positioned towards a middle point of the pipe, in other aspects the sensing surface 10 may be positioned towards the inner-wall of the pipe.

In an embodiment of the present invention, when the specific fluid contacts the sensing surface 10, the specific fluid may form a deposition layer 30 of the specific fluid on the sensing surface 10. The specific fluid may displace other fluids from contacting the sensing surface 10 and/or may spread over the entire surface of the sensing surface 10 exposed to the flowing fluid 20.

In an embodiment of the present invention, the amount of the specific fluid deposited on the sensing surface 10 may be proportional to the amount/concentration of the specific fluid in the flowing fluid 20. In certain aspects of the present invention, the specific fluid may be a contaminant or the like. Merely by way of example, the flowing fluid 20 may be water and the specific fluid may be oil. In such an example, the sensing surface 10 may be a strongly oil-wettable material such as polytetrafluoroethylene ("PTFE") or the like.

In an embodiment of the present invention, the rate of change of the amount of the specific fluid deposited on the sensing surface 10 may be determined. This rate of change is proportional to the concentration of the specific fluid/specific dispersed phase in the flowing fluid 20. As such, the concentration of the specific fluid in the flowing fluid 20 may be measured/monitored by measuring/monitoring the rate of change of the deposition on the specific fluid/specific dispersed phase on the sensing surface 10. However, such measuring/monitoring may only be applicable to low concentrations of the specific fluid since high concentrations may swamp/overwhelm the wetting effect.

Figure 2:
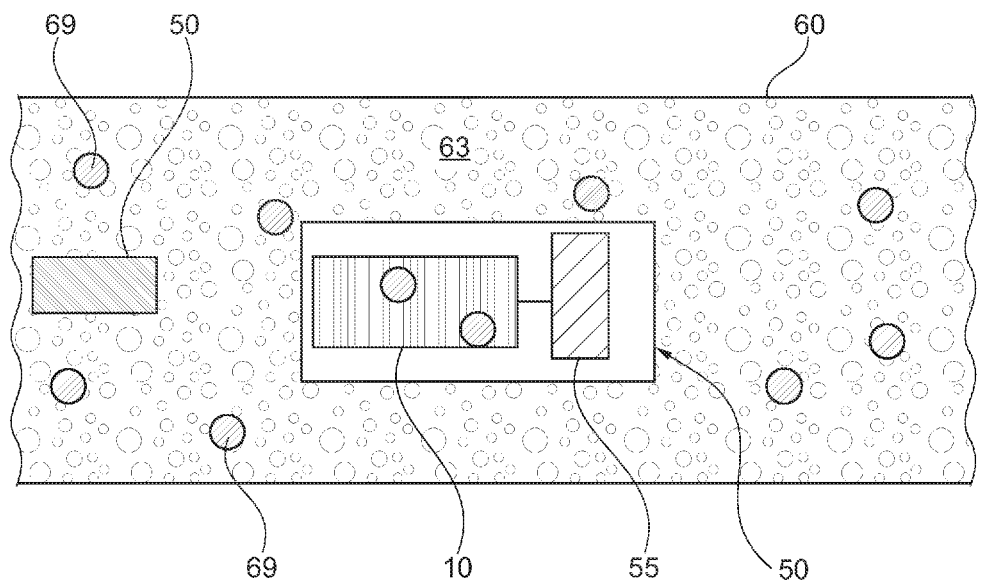
FIG. 2 is a schematic-type diagram of a concentration sensor for determining a concentration of a dispersed phase in a fluid, in accordance with an embodiment of the present invention.

FIG. 2 is a schematic-type diagram of a concentration sensor for determining a concentration of a dispersed phase in a fluid, in accordance with an embodiment of the present invention. In an embodiment of the present invention, a concentration sensor 50 may be coupled with a conduit 60 to provide that the sensing surface 10 of the sensor 50 contacts a fluid 63 flowing through the conduit 60. Merely by way of example, the conduit may be a pipeline or the like or a sampling conduit attached to a pipeline through which a sample of the fluids flowing in the pipeline is diverted for testing. Again, merely by way of example, the pipeline may be associated with an industrial process and the fluids flowing in the conduit 60 may be being tested for environmental compliance.

In some embodiments of the present invention, the monitoring of the dispersed phase may be performed on a fluid that is static. In such an embodiment, to provide for flow of the static fluid over the concentration sensor 50, a flow imparting device (not shown) may be used to cause flow of the static fluid. The flow imparting device may comprise a pump, a propeller, an impeller or the like. The flow imparting device may be controlled to provide the static fluid with a known/desired flow rate over the concentration sensor 50. Use of the flow imparting device may provide for operation of embodiments of the present invention in reservoirs or the like where flow of the contained fluid may be less than needed for operation of the concentration sensor 50.

The concentration sensor 50 may comprise the sensing surface 10 and a monitoring device 55. As the fluid 63 flows through the conduit 60, the fluid 63 may come into contact with the sensing surface 10. In an embodiment of the invention, the sensing surface 10 may be selected to be strongly wettable by a dispersed phase 69 in the fluid 63. As such, when the dispersed phase 69 is present in the fluid 63 and contacts the sensing surface 10, the dispersed phase 69 may form a deposit on/wet the sensing surface 10. In this way, the sensor 50 may be configured to be specifically/preferentially wettable by the dispersed phase 69.

In an embodiment of the present invention, the monitoring device 55 may be configured to determine an amount of the dispersed phase 69 collected on the sensing surface 10 and/or a rate of change of the deposition of the dispersed phase 69 on the sensing surface 10. The monitoring device 55 may comprise an optical-fluid analyzer, an ultrasonic system, a mass analyzer, a conductivity analyzer, resistivity analyzer, a capacitance analyzer, a Doppler analyzer, a microwave analyzer, a spectral analyzer and/or any device capable of producing an output that may vary with respect to changes in the mass, dimensions and/or other physical or chemical properties of the dispersed phase 69 deposited on the sensing surface 10. Merely by way of example, the sensing surface 10 may be optically or electrically interrogated and changes in the spectral characteristics or electrical characteristics of the sensing surface 10 may correlate to an amount/change in amount of the dispersed phase 69 on the sensing surface 10. In an aspect of the present invention, an output from the monitoring device 55 may be provided to a processor (not shown) that may process the output to provide for detection/monitoring of the dispersed phase 69 and/or determination of a relative concentration of the dispersed phase 69 in the flowing fluid 63.

In some aspects of the present invention, a ratio of the dimensions of the sensing surface 10 with regard to the cross-sectional area of the conduit 60 may be used to process a concentration of the dispersed phase 69 in the fluid 63. In certain aspects, the flow imparting device may be used to cause a static fluid to become the flowing fluid 63. The flow imparting device may be used in conjunction with the conduit 60 to provide for a flow of the flowing fluid 63 over the concentration sensor 50. Such embodiments may be used to measure reservoirs or large bodies of fluids, fluid not flowing in a pipe/conduit and/or fluids flowing slowly through a pipe/conduit.

A flowmeter (not shown) may be used to measure a flow rate of the fluid 63 in the conduit 60 and this may be used in conjunction with the output from the monitoring device 55 to process a concentration of the dispersed phase 69 in the fluid 63. Modeling, theoretical analysis, experimentation, prior use of the sensor 50 and/or the like may be used in processing the concentration of the dispersed phase 69 in the fluid 63 from the output of the monitoring device 55. In some embodiments of the present invention, the sensor 50 may be tested in a pipe of known dimensions with a flowing fluid containing a known concentration of a dispersed phase to provide for determining a normalization factor for the sensor 50.

Figure 3A:
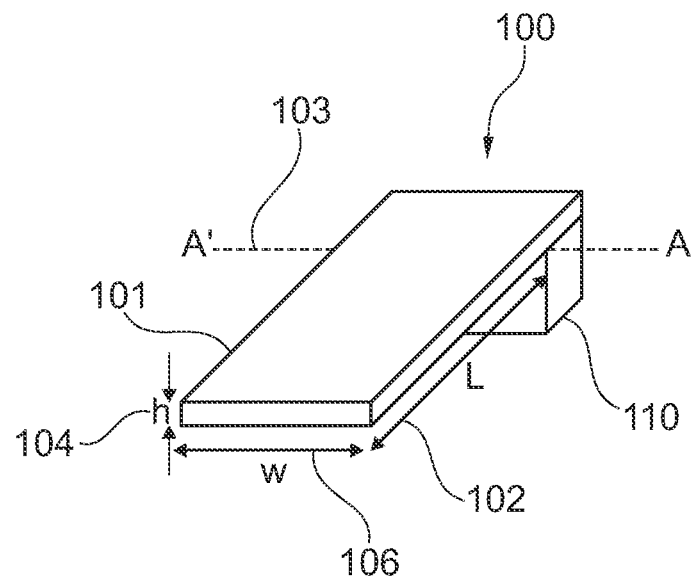
FIG. 3A illustrates a vibrating sensor for determining presence/concentration of a dispersed phase in a fluid, in accordance with an embodiment of the present invention.

FIG. 3A illustrates a vibrating sensor for determining/monitoring of a presence/concentration of a dispersed phase in a fluid, in accordance with an embodiment of the present invention. In an embodiment of the present invention, a vibrating sensor 100 may comprise a sensing element 101 coupled with a base 110: The base 110 may comprise a transducer (not shown) that may be used to vibrate the sensing element 101. The vibrations of the sensing element 101 may in some aspects of the present invention be ultrasonic in nature. Merely by way of example, the transducer may comprise a piezoelectric element, a magnetostrictive element or the like. In some aspects, the transducer may provide for generating a sinusoidal displacement of the sensing element 101.

The sensing element 101 may comprise a width (w) 106, a length (l) 102, where the length (l) 102, extends beyond the base 110 and a height (h) 104. In some embodiments of the present invention, the sensing element 110 may be cantilevered from the base 110 and may be set into oscillation about a line AA' 103. The natural (primary mode) resonant frequency of oscillation (in a vacuum) of the sensing element 101 may be given by:

$$\omega_0 = k_1 \frac{h}{L^2} \sqrt{\frac{E}{\rho}}$$

where E is the Young's modulus and $\rho$ the density of the sensing element 101. The constant of proportionality is given by:

$$k_1 = \frac{1.8751^2}{2\sqrt{3}} = 1.01$$

When the sensing element 101 is surrounded by/in contact with an infinite fluid of density $\rho_L$, the oscillation frequency of the sensing element 101 is reduced to $\omega_L$. Merely by way of example so as to provide for understanding of possible dynamics of embodiments of the present invention, when the length (l) 102 is 10 mm, the height h 104 is 0.05 mm, the density of the sensing element $\rho_S$ will be 7810 kg/m$^3$ and the Young's modulus of the sensing element 101 E will be 860 GPa. In such an example, the resonant frequency in a vacuum, $\omega_0$, of the described system will be 5325 rad/s. For such an example, if the liquid surrounding/in contact with the sensing element 101 has a density $\rho_L$ of 1000 kg/m$^3$ then the resonant frequency of the vibrating element is reduced as a result of contact with the liquid to a resonant frequency of $\omega_L$ equal to 5261 rad/s.

Figure 3B:
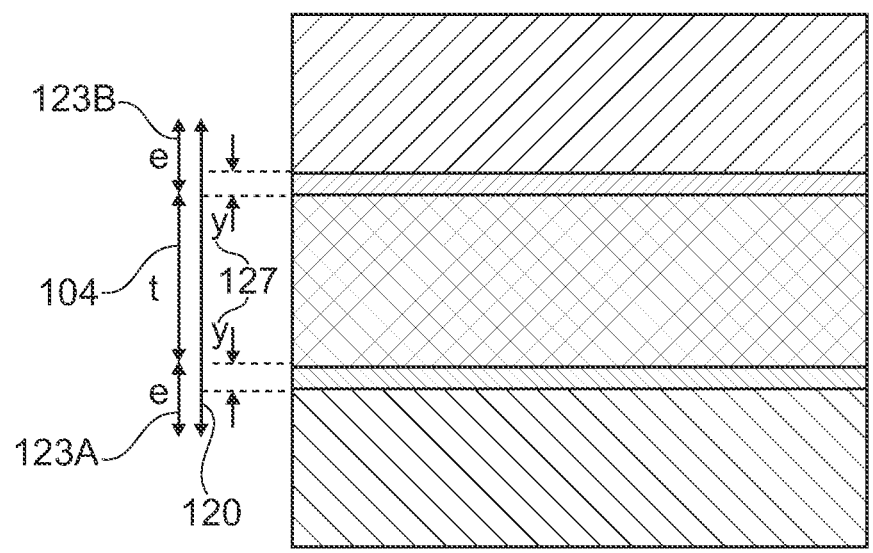
FIG. 3B illustrates contamination of a sensing element of the vibrating sensor of FIG. 3A, in accordance with an embodiment of the present invention.

FIG. 3B illustrates contamination of a sensing element of the vibrating sensor of FIG. 3A, in accordance with an embodiment of the present invention. Though in theory, the vibrating sensing element 101 has an influence to infinity, in aspects of the present invention, the sensing element 101 may be vibrated with a high frequency and a small amplitude to provide that the effective interaction with the liquid surrounding the sensing element 101 may be confined to a small distance from the sensing element 101. In aspects of the present invention, the amplitude of vibration may be controlled to provide the desired interaction between the sensing element 101 and the surrounding liquid. Changes may be made due to the viscosity of the liquid, the operating condition etc. Neglecting edge effects, when the sensing element 101 is surrounded by liquid it may be considered to have a new thickness 120 comprising the height (h) 104 and liquid layers 123A and 123B of thickness or extent (e). Furthermore, the liquid layers 123A and 123B may contribute to the mass of the sensing element 101 and not to the restoring force. Such a system may provide that:

$$\omega_L = k_1 \frac{h}{L^2} \sqrt{\frac{E}{\rho_s + \frac{2e}{h}\rho_L}}$$

hence $$\frac{\omega_0}{\omega_L} = \sqrt{1 + \frac{2e}{h}\frac{\rho_L}{\rho_S}}$$

where for certain aspects of the present invention $e\rho_L << h\rho_S$ and thus $$\frac{\omega_0 - \omega_L}{\omega_0} \approx \frac{e}{h}\frac{\rho_L}{\rho_S}$$

Merely by way of example, inserting the numbers for water in the equation above, provides that e~0.0047 mm or about 5 microns and Applicants have determined that this is thin enough to provide that the approximation $e\rho_L << h\rho_S$ of certain aspects of the present invention is reasonable.

In embodiments of the present invention, only fluid in this boundary layer, comprising liquid layers 123A and 123B, may influence the frequency of the sensing element 101. In embodiments of the present invention where the vibrating sensor 100 is being used to measure the density of a fluid of interest surrounding the sensing element 101, when the probe is wetted by a contaminant fluid dispersed in the fluid of interest, the contaminant fluid will provide part of the liquid layers 123A and 123B and will thus affect the vibrational frequency of the sensing element 101. For example, if the contaminant fluid is considered to have a density ($\rho_c$) and to wet the sensing element 101 with a layer having a thickness (y) 127, then the density measured by the vibrating sensor 100 will comprise the volume averaged density of the wetted layer of the contaminant fluid and the fluid of interest over the thickness of the liquid layers 123A and 123B, (e).

The effective density $\rho_E$ of this combination of liquids in the liquid layers 123A and 123B may be found from:

$$\rho_E e = \rho_L(e-y) + \rho_c y$$

hence $$\rho_E = \rho_L + \frac{y}{e}(\rho_c - \rho_L)$$

In one aspect of the present invention, the density of the fluid of interest $\rho_L$ is known and the density of the contaminant $\rho_c$ is also known. For example, in an embodiment of the present invention, if the vibrating sensor 100 is being used to detect the presence of or the concentration of oil contaminants in water that is being sought to be returned to the environment, the densities of the fluid of interest, water, and the contaminant to be measured, oil, will be known. In such an embodiment, the difference between the density of the liquid of interest measured by the vibrating sensor and the known density of the liquid of interest may be processed to obtain a value of the thickness of the layer of the contaminant fluid wetting the sensing element 101.

In another aspect of the present invention, the relative density of the fluid of interest $\rho_L$ to the density of the contaminant $\rho_c$ may be known. For example, in an embodiment of the present invention, if the vibrating sensor 100 is being used to detect the presence of or the concentration of oil contaminants in water that is being sought to be returned to the environment, the relative densities of the fluid of interest, water, and the contaminant to be measured, oil, will be known. In an embodiment of the present invention, the relative density may be processed to obtain a value of the thickness of the layer of the contaminant fluid wetting the sensing element 101. In an aspect of the present invention, where the rate of change of the layer of the contaminant fluid wetting the sensing element 101 is used to process a value for or the actual concentration of the dispersed phase only an estimate of the relative densities of the fluid mixture and the dispersed phase may be necessary. For example, different hydrocarbons and even different types of oils may have different densities and one of these densities may be enough or even an estimate of one of these densities may be enough in calculating a relative density for a determination of the concentration of the dispersed phase.

Figure 3C:
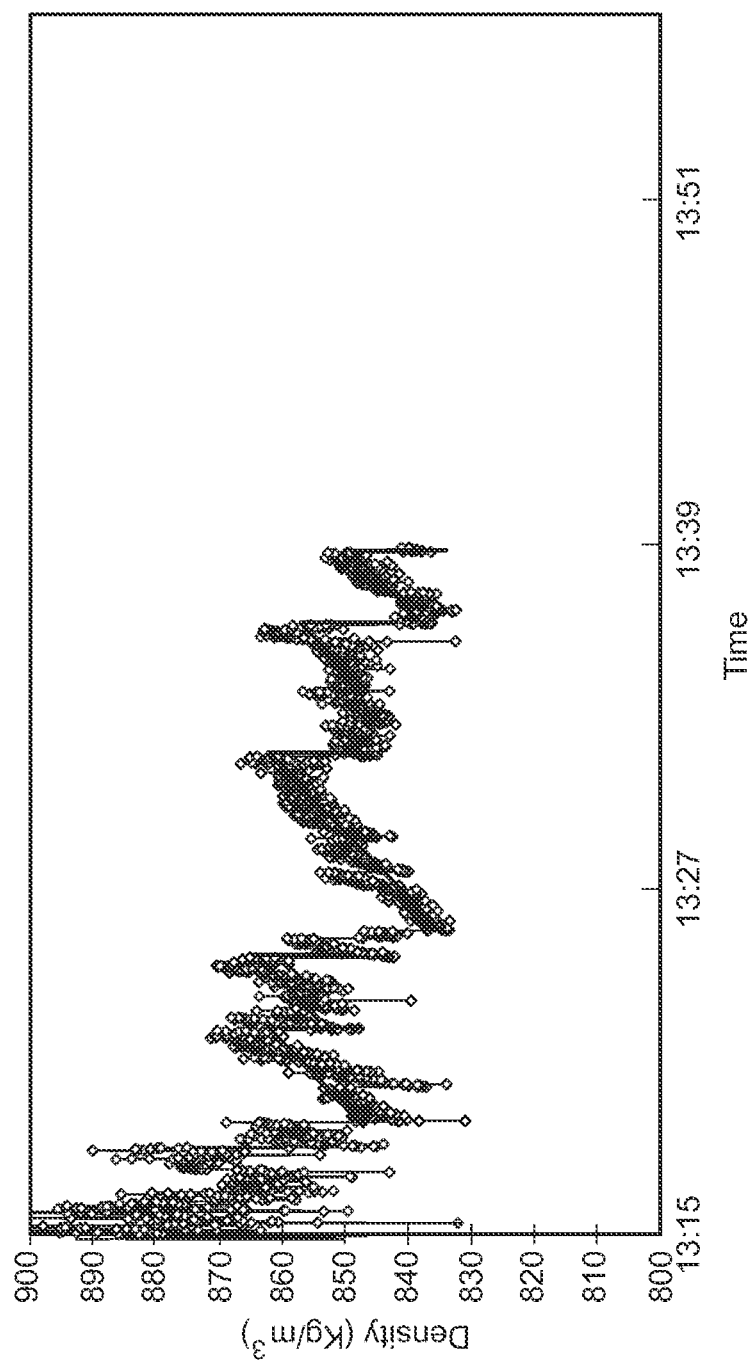
FIG. 3C illustrates an output from the vibrating sensor of FIG. 3A for a flow of oil over the vibrating sensor, in accordance with an embodiment of the present invention.

FIG. 3C illustrates an output from the vibrating sensor of FIG. 3A for a flow of oil over the vibrating sensor, in accordance with an embodiment of the present invention. In FIG. 3C, the fluid flowing past the sensing element 101 is clean oil. In accordance with the present invention, the output illustrated in FIG. 3C shows the slow accumulation of water, the dispersed phase in the clean oil being tested for/monitored in FIG. 3C, on the sensing element 101 of the sensor due to wetting followed by the sudden release of a portion of the water from the sensing element 101 resulting in a thinner layer on the sensing element 101; the minimum amount of the water on the sensing element being a residual wetting water film.

Considering the sawtooth type feature of the illustrated output around the time (13:27), the measured density from the sensor changes from 833 kg/m³ to 862 kg/m³ in about 356 seconds. From this information, in accordance with aspects of the present invention, the minimum water film thickness may be found to be about 0.61 microns and the maximum water film thickness before detachment is about 1.37 microns. As such, in an embodiment of the present invention, by processing the output from the vibrating sensor 100, the thickness of the layer of a contaminant that wets the sensing element 101 may be determined. For example, in certain aspects of the present invention, the sensing element 101 may be selected to be wetted by water and may be placed in an oil flow. In such aspects, any dispersed water in the oil will wet the sensing element 101 creating deposition/wetting of a layer of water on the sensing element 101. As such, the output from the vibrating sensor 100 may be processed to determine a thickness of the water layer on the sensing element 101 and/or the rate of change of the thickness of the water layer. In other embodiments, the flow may be a water flow and the dispersed phase may be oil.

Figure 3D:
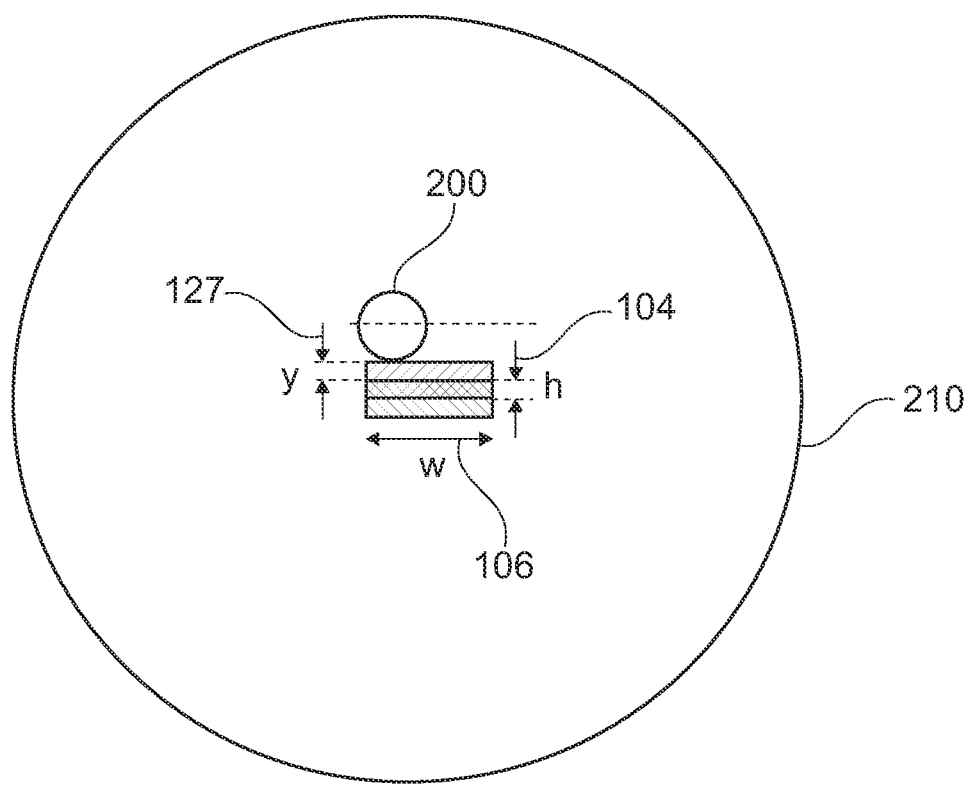
FIG. 3D is a schematic-type illustration of interaction between a dispersed contaminant in a fluid and the vibrational sensor of FIG. 3A, in accordance with an embodiment of the present invention.

FIG. 3D is a schematic-type illustration of interaction between a dispersed contaminant in a fluid and the vibrational sensor of FIG. 3A, in accordance with an embodiment of the present invention. In an embodiment of the present invention, by assuming a streamline flow of a "clean" liquid such as oil around the wetted probe, a water flux in the "clean" oil flow may be determined by processing the water flux necessary to increase the water film thickness by the amount that may be processed from the output from the vibrating sensor 100. In an embodiment of the present invention, the flux may be calculated by assuming the water to be dispersed in the oil in the form of droplets 200 of diameter d. In such an embodiment, the concentration of such droplets in the fluid may be processed using the dimensions of a pipe 210 through which the fluid is flowing (made to flow) and a flow rate of the fluid in the pipe 210.

In a perfect coalescence process, every droplet in a capture area will coalesce on the sensing element, wherein the capture area ($A_{Capture}$) may be defined as the area w(h+2y+d); where (w) is the width (w) 106, (h) is the height h 104, (y) is the thickness of the wetting layer (y) 127 and (d) is the diameter (d) of the droplet 200. In the perfect coalescence process the droplet 200 will add to the water film wetting the surface of the sensing element 101 spreading out instantly on impact.

Merely by way of example, if the concentration of water in oil is C ($m^3/m^3$), the pipe area is $A_{Pipe}$ and the flow rate Q, then the volumetric flux of water onto the probe is given by:

$$CQ_w(h+2y+d)/A_{Pipe}.$$

This flux spreads out over the probe surface (upper and lower) area 2wL and thus the rate of change of the water film thickness is given by:

$$\frac{dy}{dt} = \frac{CQw(h+2y+d)}{A_{Pipe}wL}$$

We already know that y<h and if the droplets are small, then this equation may be reduced to $$\frac{dy}{dt} = \frac{CQh}{A_{Pipe}L}$$

In an embodiment of the present invention, from analysis of the output from the vibrating sensor 100 the value of dy/dt may be measured. Thus, in such an embodiment, the concentration of the contaminant fluid in the main flowing fluid can be found, where the concentration C is given by the following:

$$C = \frac{\frac{dy}{dt}A_{Pipe}L}{Qh}$$

In an embodiment of the present invention where a concentration of oil in water is to be measured, the sensing surface 101 may be made oil wetted. In certain aspects, for measuring concentrations of a dispersed phase in a main fluid flow, such as for oil-in-water, water-in-oil or the like, an assumption of uniformly dispersed contaminants may be good for small droplets and dilute contamination. In such aspects of the present invention, the exact location of the sensor in the flow does not matter. Some embodiments of the present invention may provide a real-time in-line concentration measurement system that is applicable for use with flows containing low concentrations of contaminants. In other embodiments, the flow may be generated to provide for concentration monitoring of static fluids or slow moving fluids and/or the like. These embodiments may provide for determining concentrations of a dispersed phased when the density of the two phases—dispersed and continuous—are known and the sensor is configured to have a sensing surface that is wetted by the dispersed phase.

In embodiments of the present invention in which the rate of change of the mass/physical dimensions of the dispersed phase coalescing on the wettable surface may be measured and offset, long term drifts may not affect the concentration measurements. Deposition of solids on the sensor may affect the functioning of the sensor, but such depositions may be slow compared to the liquid film growth and detachment. In certain aspects of the present invention, the sensing element 101 of the vibrating sensor 100 may be cleaned of solid depositions by using the transducers to operate the vibrating probe 100 at a high ultrasonic rate. In some embodiments of the present invention, the geometry of the vibrating sensor 100, the sensing element 101 and/or the like may be configured to optimise sensitivity for droplet capture and/or film release.

In an embodiment of the present invention, the concentration measurement process may require knowledge of the physical geometry and flow rate and the densities of the continuous and contaminant phase. However, in an embodiment in which the concentration is derived from the derivative of the film thickness with time, no calibration is necessary. The accumulation of the film on the probe also means that the measurement may in some aspects be made over a long period of time (minutes). Such aspects of the present invention may allow for low concentrations of a dispersed phase to be measured, limited only by the inherent long-term stability of the probe and its electronics. Higher concentrations may be measured in other aspects, but a point will be reached where a single droplet could "flood" the surface and flow straight off affecting the accuracy of the system. High dispersed phase concentrations tend to have larger and broader droplet size distributions.

Merely by way of example, applications of a dispersed phase oil-in-water monitor for low concentrations in accordance with an embodiment of the present invention may include produced water disposal, produced water reinjection, pipeline contamination, reservoir contamination etc. Again, merely by way of example, further applications may include first detection of water in oil and gas/condensate wells.

In some aspects of the present invention, two sensors in accordance with embodiments of the present invention may be disposed in a fluid, one preferentially water wettable and the other preferentially oil wettable. In such aspects, signal differencing may be used to eliminate zero drift—e.g. velocity or temperature effects—and may provide an improved first detection of either oil or water and/or concentration measurement device.

Whilst the above analysis has mainly concentrated on a vibrating element density/viscosity meter, the same principle of contaminant accumulation on a probe may also be applied to most other fluid probe technologies. For example, by selecting a wettable surface in accordance with aspects of the present invention, thin water films may be accumulated and detected on capacitive/microwave/electrical impedance water in oil sensors or by selecting a wettable surface in accordance with aspects of the present invention thin oil films may be accumulated and detected on optical oil in water sensors. Suitable coatings and cleaning strategies (pure hydrodynamic or external active) of such sensors may allow first detection of a contaminant and the rate of change of attached contaminant to provide for measuring/monitoring the concentration of the contaminant, in accordance with an embodiment of the present invention.

Figure 4A:
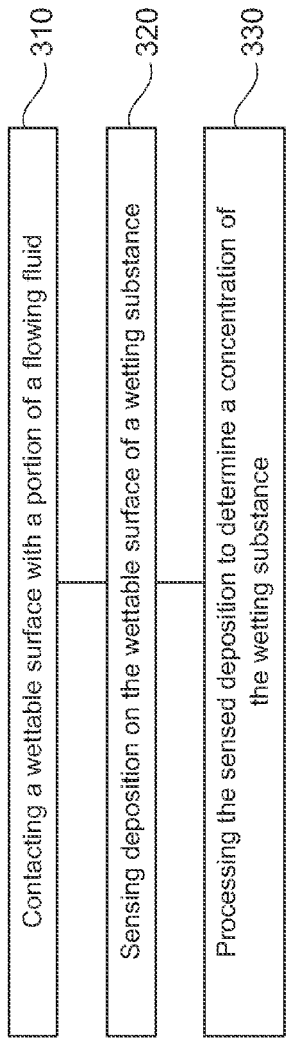
FIG. 4A is a flow-type diagram of a method for determining an inline concentration of a dispersed phase in a flowing fluid, in accordance with an embodiment of the present invention.

FIG. 4A is a flow-type diagram of a method for determining a concentration of a dispersed phase in a fluid, in accordance with an embodiment of the present invention. In step 310, a wettable surface may be contacted with a portion of a flowing fluid. The fluid may be an actively flowing fluid, i.e. a fluid flowing in a conduit, or may be a static fluid that is driven into motion by a flow generating system. For example, a static body of fluid may become contaminated by entry of contaminant fluids into the body and an embodiment of the present system, in which the static fluid is flowed over a sensing surface, may be used to monitor changes in contamination concentrations of the fluid.

The fluid may be a fluid containing a dispersed phase of interest, for example water from a hydrocarbon production or transportation system that contains a dispersed amount of oil. In such situations, the water may be monitored inline, as the water flows through a conduit, so that the concentration of oil in the water may be monitored in real-time as this may provide for fast and efficient disposal of the water in accordance with environmental regulations and principles without time intensive and expensive sample removal and testing. Alternatively, a flow generating system may be used to cause a static or slow moving fluid to flow periodically over the wettable surface, where the flow generating system may be activated on demand or configured to activate periodically.

In step 310, the wettable surface may be selected and/or configured to provide for selective wetting by a dispersed phase of interest. Again, merely by way of example, the wettable surface may be selected and/or configured to be highly wettable by oil so as to provide for wetting of the wettable surface by dispersed oil flowing in the fluid.

In step 320, the deposition/contamination on the wettable surface may be sensed. When the wettable surface is selected to be highly wettable by a specific substance, the deposition/contamination may mainly comprise of the specific substance. However, because the fluid may only contain a small fraction of the specific fluid a baseline amount of deposition on the wettable surface may initially be generated by the main component of the fluid or the like. Over time, the specific fluid may act to displace other fluids from the wettable surface and may become the main deposit/contaminant on the wettable surface. In embodiments of the present invention, sensing of the rate of deposition/contamination of the wettable surface may be made by numerous different methods such as by electrical sensing—including but not limited to monitoring resistance/conductivity associated with the wettable surface, using a capacitance analysis and/or the like—optical sensing, vibrating the wettable surface and monitoring a vibrational frequency of the wettable surface, Doppler/sonic interrogation across the deposit/contamination and/or the like.

In one embodiment of the present invention, the wettable surface may be driven to vibrate in the flowing fluid. In such an embodiment, the wettable surface may be driven by a transducer or the like that may comprise a piezoelectric transducer, magnetostrictive transducer or the like. In some aspects, the wettable surface may be an element of a microelectromechanical system ("MEMS"). When the wettable surface is driven to vibrate at a constant rate in the fluid, any changes in the vibrational frequency of the settable surface may be due to changes in the fluid properties of the wettable surface and/or the build up of the dispersed fluid on the wettable surface.

In aspects of the present invention, the fluid may comprise substantially a single liquid containing the dispersed fluid to be monitored. Merely by way of example, the flow may comprise substantially water with a dispersed phase of oil and or oil with a dispersed phase of water. In such aspects, the properties of the fluid may remain essentially constant and changes in the vibrational frequency of the wettable surface may correspond to changes in the amount/thickness of the dispersed phase wetting the wettable surface. Furthermore, even where changes in the property of the fluid may affect the vibrational frequency of the wettable surface, the changes to the frequency of the wettable surface caused by deposition of the dispersed phase on the wettable surface may be separable/distinct. In an embodiment of the present invention, an amount and/or a rate of change of the dispersed fluid on the wettable surface may be processed from the frequency of vibration of the wettable surface.

In step 330, a processor or the like may process the sensed deposition to determine a concentration of the wetting substance. In certain aspects, an amount, thickness and/or other parameter related to the physical measure of the deposition/contamination sensed on the wettable surface and or the rate of change of the deposition/contamination may be interpolated to determine an amount of a dispersed phase in the fluid. In other aspects, the rate of change of the physical amount of the dispersed phased deposited on the wettable surface may be processed to determine a concentration of the dispersed phase flowing in the fluid being tested. The rate of change of the physical amount of the dispersed phase on the wettable surface may comprise a film or the like on the wettable surface that grows to cover the wettable surface and/or expand in thickness as more of the dispersed phase wets the wettable surface. At some point, the dispersed fluid on the wettable surface may attain unsustainable proportions and the majority of the dispersed fluid deposited on the wettable surface may become detached from the wettable surface. After disassociation of the majority of the dispersed phase from the wettable surface, build-up of a deposit on the wettable surface may recommence at a rate proportional to the concentration of the dispersed phase in the flowing fluid.

In certain aspects of the present invention, a flow meter may be positioned in the flowing fluid to monitor flow rates of the flowing fluid. The flow rates from the flow meter may be output to the processor and may be used to process the concentration of the dispersed phase since the rate of deposition of the dispersed fluid on the wettable surface may be proportional to the flow rate of the fluid.

In some aspects, the concentration of the dispersed fluid contained in the flowing fluid may be based at least in part upon the surface area of the wettable surface in comparison to a cross-sectional area of a conduit through which the fluid is flowing. The processing of concentration of the dispersed fluid may be processed from the sensed physical amount of the dispersed fluid on the wettable surface and/or the rate of change of the physical amount of the dispersed fluid on the wettable surface from modeling analysis, theoretical analysis, experimentation, previous results, normalization with other concentration measurements, normalization with known concentration levels and/or the like.

Figure 4B:
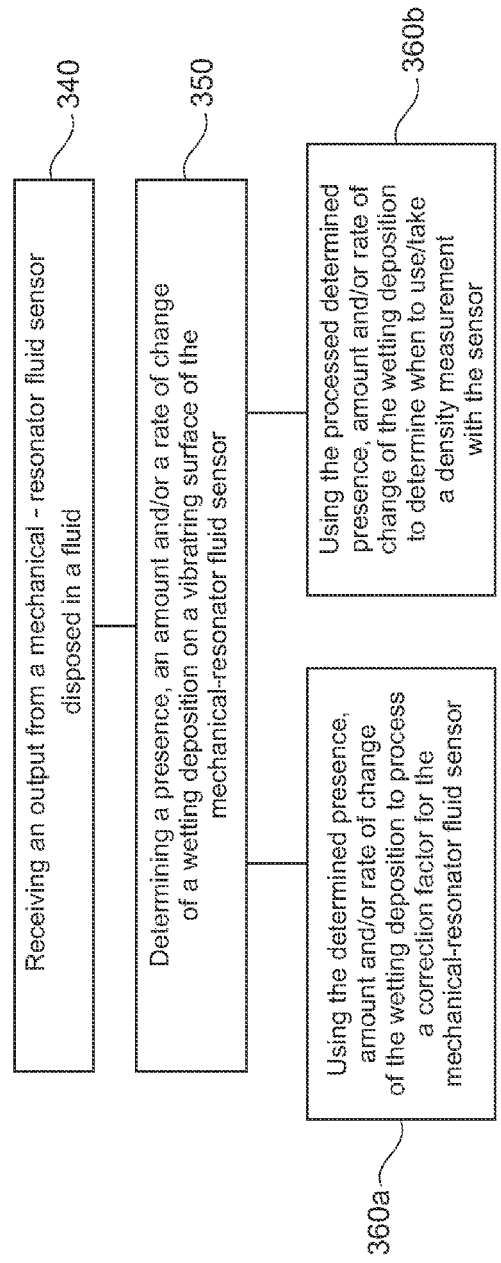
FIG. 4B is a flow-type diagram of a method for correcting a mechanical-resonator-type fluid sensor, in accordance with an embodiment of the present invention.

FIG. 4B is a flow-type diagram of a method for correcting a mechanical-resonator-type fluid sensor, in accordance with an embodiment of the present invention. In step 340, an output from a mechanical-resonator fluid sensor disposed in a fluid may be received. The mechanical resonator fluid sensor may comprise a mechanical system in which a portion of the system contacts a portion of a fluid to be analyzed/monitored and is made to vibrate. In such systems, for example, when a constant vibrational drive is applied to the vibrating portion the frequency of vibration or the like may vary in accordance with the properties of the fluid, such as the density, viscosity and or the like of the fluid. In certain aspects the mechanical-resonator fluid sensor may be a micro-electromechanical system ("MEMS") or the like.

In step 350, a presence, amount and/or rate of change of the wetting deposition on the vibrating element of the mechanical-resonator may be determined. Such a determination may be provided by a sensor such as the sensors described above or changes in the vibrational frequency of the vibrating elements. In an aspect of the present invention, the vibrational frequency of the vibrating element may undergo periodic changes—slowing down as a wetting fluid builds up on the vibrating element, speeding up when the wetting fluid becomes unstable on the vibrating element and peels away from the vibrating element and then slowing down again as the wetting fluid builds up on the vibrating element.

In step 350, the rate of change of the dispersed fluid present on the wettable surface may be determined by measuring a change in properties of an electromagnetic beam/signal transmitted in to the dispersed phase present on the wettable surface. For example, a microwave, optical, ultraviolet, infrared signal and/or the like may be transmitted into the dispersed phase present on the wettable surface and the change in transmission and/or absorption of the signal may be measured. In other aspects, a change in electrical properties, such as conductance, impedance, resistance, capacitance and/or the like may be measured to determine the rate of change of the dispersed phase present on the wettable surface.

In other aspects, in step 350, acoustic properties, changes in acoustic properties may be measured to determine the rate of change of the dispersed phase present on the wettable surface, for example changes in an ultrasonic beam transmitted into/through the dispersed phase present on the wettable surface may be monitored. In some aspects of the present invention, exiting sensors may be modified to be concentration monitors in accordance with the present invention by making a sensing surface of the existing sensor selectively wettable by a dispersed phase to be monitored and using the sensor to measure the rate of change of the dispersed phase present on the sensing surface.

In step 360*a*, the determined presence, amount and/or rate of change of the wetting deposition may be used to process a correction factor for the mechanical-resonator fluid sensor. In certain aspects, because the mechanical-resonator sensor uses frequency of vibration of the vibrating element to determine properties of the fluid, changes to the vibration frequency of the vibrating element due to wetting may cause errors in the determined properties. In an embodiment of the present invention, by sensing presence, amount and/or rate of change of the wetting deposition, correction factors may be applied to correct for the presence/amount of the wetting of the vibrating element. Moreover, in an embodiment of the present invention, because the wetting of the vibrating element may be periodic in nature, changes in frequency of the vibrating element caused by wetting may be identified and removed from the frequency-output—signal for the vibrating element. Thus, increasing the accuracy and performance of the mechanical-resonator sensor.

In step 360*b*, the processed determined presence, amount and/or rate of change of the wetting deposition may be used to determine when to use/take a fluid measurement, such as a density measurement, viscosity measurement and/or the like with the sensor. In an embodiment of the present invention, by monitoring the amount or presence of wetting of the vibrating surface, a determination can be made to process a measurement from the mechanical-resonator sensor when the amount of wetting of the vibrating element is known, is a minimum and/or the like. In this way, the accuracy of the mechanical-resonator sensor may be increased.

While the principles of the disclosure have been described above in connection with specific apparatuses and methods, it is to be clearly understood that this description is made only by way of example and not as limitation on the scope of the invention.

What is claimed is:

1. A method for monitoring a dispersed phase in a flowing immiscible fluid mixture, comprising:
   measuring a flow rate of the flowing immiscible fluid mixture;
   contacting a wettable sensing surface with a flowing portion of the fluid mixture, wherein the wettable sensing surface is configured to be preferentially wettable by the dispersed phase;
   oscillating the wettable sensing surface in the flowing portion of the fluid mixture at a resonant frequency;
   measuring a rate of change of frequency of oscillation of the wettable sensing surface in the flowing portion of the fluid mixture;
   using the rate of change of frequency of oscillation of the wettable sensing surface to determine a rate of change of the amount of the dispersed phase wetting the wettable sensing surface; and
   using the rate of change of the amount of the dispersed phase wetting the wettable sensing surface and the flow rate to determine a concentration of the dispersed phase in the flowing portion of the fluid mixture.

2. The method for monitoring the dispersed phase in accordance with claim 1, wherein the sensing surface is disposed within a conduit and the portion of the fluid mixture flows through the conduit.

3. The method for monitoring the dispersed phase in accordance with claim 2, wherein the conduit is configured for transporting hydrocarbons.

4. The method for monitoring the dispersed phase in accordance with claim 2, wherein the conduit is configured for transporting water.

5. The method for monitoring the dispersed phase in accordance with claim 2, wherein the wettable sensing surface has a length of the order of 10 millimeters.

6. The method for monitoring the dispersed phase in accordance with claim 2, wherein the wettable sensing surface has a height of the order of 0.05 millimeters.

7. The method for monitoring the dispersed phase in accordance with claim 1, wherein the step of using the rate of change of the amount of the dispersed phase wetting the wettable sensing surface and the flow rate to determine a concentration of the dispersed phase in the flowing portion of the fluid mixture comprises using relative densities of fluids in the flowing immiscible fluid mixture to determine the concentration of the dispersed phase.

8. The method for monitoring the dispersed phase in accordance with claim 1, wherein determining the concentration of the dispersed phase comprises using a cross-sectional area of the wetting surface to determine the concentration.

9. The method for monitoring the dispersed phase in accordance with claim 1, wherein determining concentration of the dispersed phase comprises disposing the sensing surface in a conduit, flowing the portion of the fluid mixture through the conduit and using a cross-sectional area of the conduit to determine the concentration.

10. The method for monitoring the dispersed phase in accordance with claim 1, wherein the sensing surface is configured to be preferentially wettable by water.

11. The method for monitoring the dispersed phase in accordance with claim 1, wherein the sensing surface comprises a hydrophilic material or is coated with a hydrophilic material.

12. The method for monitoring the dispersed phase in accordance with claim 1, wherein the sensing surface is configured to be preferentially wettable by oil.

13. The method for monitoring the dispersed phase in accordance with claim 1, wherein the sensing surface comprises a hydrophobic material or is coated with a hydrophobic material.

14. The method for monitoring the dispersed phase in accordance with claim 1, wherein the sensing surface comprises polytetrafluoroethylene.

15. The method for monitoring the dispersed phase in accordance with claim 1, further comprising:
- vibrating at least a portion of the sensing surface at an ultrasonic frequency to remove at least a portion of the dispersed phase.

\* \* \* \* \*